(12) United States Patent
Buckley et al.

(10) Patent No.: US 10,711,948 B2
(45) Date of Patent: Jul. 14, 2020

(54) ROTARY INTRODUCER

(71) Applicant: Sparc Systems Limited, Malvern, Worcestershire (GB)

(72) Inventors: David Buckley, Malvern (GB); David Reynolds, Malvern (GB); Jonathan Ives, Malvern (GB)

(73) Assignee: Sparc Systems Limited (GB)

( * ) Notice: Subject to any disclaimer, the term of this patent is extended or adjusted under 35 U.S.C. 154(b) by 330 days.

(21) Appl. No.: 15/830,521

(22) Filed: Dec. 4, 2017

(65) Prior Publication Data
US 2018/0156391 A1    Jun. 7, 2018

(30) Foreign Application Priority Data

Dec. 5, 2016 (GB) .................................. 1620678.1

(51) Int. Cl.
*F17D 3/01* (2006.01)
*F17D 1/08* (2006.01)
(Continued)

(52) U.S. Cl.
CPC ................ *F17D 3/01* (2013.01); *A22C 17/10* (2013.01); *F16L 37/004* (2013.01); *F16L 55/46* (2013.01);
(Continued)

(58) Field of Classification Search
CPC ......... F16L 37/004; F16L 41/16; F16L 55/46; F16L 55/48; F16L 2201/40; A22C 17/10; F17D 1/08
See application file for complete search history.

(56) References Cited

U.S. PATENT DOCUMENTS 3,715,055 A * 2/1973 Kendrick et al. ...... B65G 53/30
                                                        221/75
4,491,177 A    1/1985 Baugh
(Continued)

FOREIGN PATENT DOCUMENTS

| EP | 2 581 169 A1 | 4/2013 |
|---|---|---|
| GB | 2340861 A | 1/2000 |
| GB | 2515319 A | 12/2014 |

OTHER PUBLICATIONS

European Search Report for EP 17 20 5272 dated Apr. 24, 2018, 4 pp.

(Continued)

*Primary Examiner* — Daniel S Larkin
(74) *Attorney, Agent, or Firm* — James A. Sheridan; Sheridan Law, LLC

(57) ABSTRACT

A rotary introducer is provided for introducing a trackable element and/or contaminant onto a flow path of a food-transit system without adjusting a flowrate. The introducer comprises an inlet and an outlet which is communicable with a food-transit conduit; and a pair of rotatable driving/drivable members. In a trackable-element receiving condition, the inlet is open to receive a trackable element in the device cavity, and the outlet is closed by at least one of the driving/drivable member. However, in a discharge condition, the outlet is open such that a trackable-element discharge force is directed radially inwardly through the outlet to discharge the trackable element from the device cavity, thus enabling outlet to close. A food-transit system using the rotary introducer and a method of introducing a trackable element and/or contaminant into food-transit system without adjusting a flowrate of foodstuffs therethrough are also provided.

20 Claims, 9 Drawing Sheets

(51) Int. Cl.
*F16L 55/46* (2006.01)
*F16L 37/00* (2006.01)
*A22C 17/10* (2006.01)
*G01N 33/02* (2006.01)

(52) U.S. Cl.
CPC ............ *F17D 1/08* (2013.01); *F16L 2201/40* (2013.01); *G01N 33/02* (2013.01)

(56) References Cited

U.S. PATENT DOCUMENTS

2011/0120499 A1   5/2011   Pruett et al.
2015/0068727 A1   3/2015   Hern et al.

OTHER PUBLICATIONS

Examination Report for GB 1620678.1 dated Jul. 19, 2017, 1 pp.
Search Report for GB 1620678.1 dated May 24, 2017, 1 pp.
English translation of EP2581169, 15 pp.

* cited by examiner

ROTARY INTRODUCER

RELATED APPLICATIONS

This application claims the benefit under 35 U.S.C. § 119(a)-(d) of British Patent Application No. 1620678.1 filed on 5 Dec. 2016, the disclosure of which is incorporated by reference.

FIELD OF THE TECHNOLOGY

The present invention relates to a rotary introducer, particularly but not necessarily exclusively for introducing a trackable element and/or contaminant onto a flow path of a food-transit system. A combination of a rotary introducer and a trackable element and/or contaminant, a food-transit system for the transit of liquid or semi-liquid foodstuffs, and a method of introducing a trackable element and/or contaminant into food-transit system without adjusting a flowrate of foodstuffs therethrough are also provided. The invention also relates to an introducer which utilises an urging mechanism to in use move the trackable element and/or contaminant on or into an associated flow path.

BACKGROUND OF THE INVENTION

Comestible products are extremely well-regulated in terms of the suitability of products for human and/or animal consumption, and in order to determine whether the products meet the regulatory requirements, the foodstuffs must be monitored. It is particularly important to monitor the foodstuffs for potentially toxic compounds and/or for foreign bodies introduced into products designated for consumption.

In certain industries, particularly those which deal with liquid or semi-liquid foodstuffs, the comestible products may be channelled through a network of pipes in order to transport the products from location to location. Typically, these pipes are opaque, and therefore optical inspection of the foodstuffs therein is not possible.

Such foodstuffs are commonly monitored by non-optical means, such as by X-ray interrogation and/or metal detection of the product as they pass a given monitoring point. By way of example, in the meat-processing industry, a slurry of meat products may contain bones, skin, hair or shot from a gun which is not desirable for consumption. X-ray interrogation is able to discern whether such foreign bodies have entered into the piped slurry.

Given the rate of throughput of comestible products through a food-transit network, contaminated product may have passed through the interrogation region prior to determination of the contamination, in which case, the user must determine where the contaminated product is. This can be estimated, based on an expected flowrate in the pipes. However, it is preferred that a non-toxic trackable element and/or contaminant be inserted into the system in order to determine whether the system can accurately detect foreign or undesirable objects of a given size at any given time To introduce such a trackable element and/or contaminant into the system, there are only two options: either the system as a whole must be shut down, and the trackable element and/or contaminant safely inserted into an inlet port; or the trackable element and/or contaminant can be inserted into an inlet port of the pipe network whilst the system is operational.

The former option is undesirable, since the efficiency of the processing of the product is drastically reduced by operation shutdown due to the time it takes the system to get back up to speed, by which point the trackable element and/or contaminant has already passed the monitoring equipment. However, the latter case is also undesirable, since opening of the inlet port results in discharge of the comestible product, which will create a mess and result in loss of productivity, especially if the product is highly pressurised.

SUMMARY OF THE INVENTION

The present invention seeks to provide a mechanism by which a trackable element and/or contaminant can be introduced into a food-transit system without requiring a full shutdown or ejecting valuable product from the system in the process.

According to a first aspect of the invention, there is provided a rotary introducer for introducing a trackable element and/or contaminant onto a flow path of a food-transit system without adjusting a flowrate, the rotary introducer comprising: an inlet for receiving a trackable element and/or contaminant; an outlet which is positioned radially inwardly of the inlet and which is communicable with a food-transit conduit to discharge the trackable element and/or contaminant thereinto; a rotatable driving member having a first device-contact surface which is movable between a driving-member start position at or adjacent to the inlet and a driving-member stop position; and a rotatable drivable member having a second device-contact surface which is movable between a drivable-member start position at or adjacent to the inlet and a drivable-member stop position at or adjacent to the outlet; the driving-member start position and the drivable-member start position being angularly displaced from each other; the driving-member stop position and drivable-member stop position being coincident or substantially coincident; the first and second device-contact surfaces opposing each other and defining a volume-adjustable device cavity; wherein, in a trackable-element receiving condition, the inlet is open to receive a trackable element and/or contaminant in the device cavity due to the first and second device-contact surfaces being at the angularly displaced driving-member and drivable-member start positions respectively, and the outlet is closed by at least one of the driving and drivable member; and in a trackable-element discharge condition, the outlet is open with the second device-contact surface being at the drivable-member stop position and the first device-contact surface being urged towards the driving-member stop position such that a trackable-element discharge force is directed radially inwardly through the outlet to discharge the trackable element and/or contaminant from the device cavity, thus enabling the first device-contact surface to continue to the driving-member stop position causing the outlet to close.

The term 'trackable element' is intended to mean a non-consumable synthetic or man-made trackable or tracking device. Such a 'trackable element' may therefore be a contaminant, since it contaminates, in a preferably non-toxic manner, the food produce on the flow path. However, the trackable element may itself be an ingestible food product, providing it can be monitored within the original produce on the flow path. As such, in this later case, the trackable element may not strictly be considered to be a 'contaminant', although its introduction will effectively cause contamination of the original food stuff even though it may itself be ingestible and digestible by a consumer without harmful effects.

The provision of rotatable members which can cover off an outlet for a food-transit conduit allows a trackable element and/or contaminant to be inserted into the conduit without egress of material in transit during the introduction. In a first condition, the trackable element and/or contaminant is receivable into the introducer whilst the outlet is closed. The rotation of the rotatable members allows the trackable element and/or contaminant to be brought into alignment with the outlet, ready for discharge, with minimal reflux of material in transit disgorging into the device cavity.

The continued rotation of the driving member urges the first and second device-contact surfaces together in such a manner so as to force the trackable element and/or contaminant through the outlet, closing the outlet in the process. By introducing the trackable element and/or contaminant into the food-transit conduit in this manner, the outlet is only open when necessary for the introduction of the trackable element and/or contaminant. This limits the ability for egress of material in transit or contamination of the material, whilst advantageously presenting a method of introducing the trackable element and/or contaminant without shutting down the food-transit system or slowing the flow therethrough. Beneficially, the foodstuffs being transported can then be monitored without requiring cessation of the transit.

Preferably, the driving member may include a drive engagement means, which may comprise a magnetically driveable portion or a driveable ring gear.

Mechanical actuation of the driving member allows for the force applied to the trackable member to be rigorously controlled and/or timed so as to be introduced into the food-transit system automatically at predetermined times.

Preferably, the drivable member may include a recess in the second device-contact surface, the driving member having an armature upon which the first device-contact surface is positioned which is receivable within the recess. Said armature may be or substantially be wedge-shaped. Optionally, the first and second device-contact surfaces may be radially convergent with respect to one another, in which case, the first and second device-contact surfaces may form a triangular wedge to create the trackable-element discharge force.

The shaping of the first and second device-contact surfaces can be advantageously created so as to assist with urging of the trackable element and/or contaminant into the food-transit conduit whilst also simultaneously closing off the outlet, limiting the possibility of reflux of transported material into the rotary introducer which might otherwise clog the device cavity. This can beneficially reduce the need for cleaning and/or maintenance of the rotary introducer.

The rotary introducer may further comprise an introducer housing which at least partially encloses the driving and/or drivable member. The introducer housing may include an inlet port which is aligned with the inlet in the trackable-element receiving condition and/or may be integrally formed with a food-transit conduit. The drivable member may also include a projecting stop, the introducer housing including a stop-receiving slot with which the stop is engagable, the stop defining the drivable-member start and stop positions The housing can help to maintain free rotation of the rotatable members therein, keeping the driving and drivable members tight to the food-transit conduit about which they are positioned. The provision of the slot and stop ensures that regardless of the rotational position of the driving member, the drivable member can always be positionable across the outlet so as to prevent or limit ingress of the material to be transported into the device cavity.

Optionally, at least one of the driving and drivable members may include one or more bearings to facilitate relative rotation therebetween. Additionally or alternatively, the driving and drivable members may be at least in part magnetically engagable, in which case, the driving and drivable members may be adapted to magnetically engage when the first device-contact surface reaches the driving-member stop position to allow counter-rotation of the rotary introducer without opening the outlet.

Magnetic engagement between the driving and drivable members ensures that the two can latch when in close proximity to one another. The rotary introducer can thus feasibly be constructed so as to require only a single drive means, which is coupled to the driving member. Consequently, synchronisation between two distinct motors, one for each of the driving and drivable members, is not required, simplifying the construction of the rotary introducer.

There may also be provided a pipe element about which the driving and drivable members are rotationally movable, the pipe element having magnetic engagement elements at opposing longitudinal ends thereof for magnetic connection to a food-transit system.

It is preferred that the rotary introducer be provided so as to be readily engagable with existing food-transit systems. This can be achieved by providing couplings, such as flanges, which are designed so as to fit with existing pipe networks. In particular, it may be desirable to introduce the trackable element and/or contaminant at or adjacent to a monitoring system of the food-transit system, such as an x-ray sensor and/or metal detector, and therefore a corresponding coupling mechanism should be considered. Magnetic interengagement allows for the rotary introducer to be readily removed or extracted for cleaning and/or maintenance.

Optionally, a reset mechanism may be provided to return the driving and drivable members to the driving-member and drivable-member start positions respectively following discharge of a trackable element and/or contaminant.

A reset mechanism may allow for the magnetic engagement between the driving and drivable members to be dispensed with, which may expand the range of materials from which the driving and drivable members can be constructed.

According to a second aspect of the invention, there is provided a combination of a rotary introducer, preferably in accordance with the first aspect of the invention, and a trackable element and/or contaminant sized to be receivable through the inlet and outlet of the rotary introducer. The trackable element and/or contaminant may be spherical. Furthermore, the driving member may be used to indirectly drive the drivable member via the trackable element and/or contaminant when moving between the trackable-element receiving condition and trackable-element discharge condition.

The trackable element and/or contaminant can be used by the driving and drivable members to transmit the rotational force between the two. This allows the driving force to be imparted without direct contact between the driving and drivable members, which can allow the formation of the volume-adjustable device cavity.

According to a third aspect of the invention, there is provided a food-transit system for the transit of liquid or semi-liquid foodstuffs, the food transit system comprising: a food-transit pipe network defining a flow path therethrough; and a rotary introducer, preferably in accordance with the first aspect of the invention, wherein the rotary introducer is introducible onto the flow path of the food-transit pipe network to permit introduction of a trackable element and/or contaminant into the flow path without adjusting a flowrate of foodstuffs through the food-transit pipe network.

The provision of a rotary introducer onto a pipe network of a food-transit system allows for the foodstuffs therein to be monitored, in particular the detection levels of and through the system, without necessitating a shut-down in the transit of foodstuffs through the system. This allows for more accurate readings to be taken of the foodstuffs, and in particular, a more effective determination of the presence of contaminants in the system in use.

According to a fourth aspect of the invention, there is provided a method of introducing a trackable element and/or contaminant into a food-transit system without adjusting a flowrate of foodstuffs therethrough, the method comprising the steps of: a] providing a rotary introducer, preferably in accordance with the first aspect of the invention, at or adjacent to an inlet to a food-transit pipe network of the food-transit system; b] inserting a trackable element and/or contaminant into a device cavity of the rotary introducer whilst in the trackable-element receiving condition; c] rotating the driving member of the rotary introducer into the trackable-element discharge condition so as to align the trackable element and/or contaminant with the outlet; and d] continuing to rotate the driving member of the rotary introducer to create the trackable-element discharge force to urge the trackable element and/or contaminant into the inlet to the food-transit pipe network and close the outlet.

Preferably, during step d] the first and second device-contact surfaces may form a wedge of decreasing area to create the trackable-element discharge force. The method may also further comprise a step e] subsequent to step d] of counter-rotating the driving member to return the rotary introducer to the trackable-element receiving condition.

According to a fifth aspect of the invention, there is provided a rotary introducer for introducing a trackable element and/or contaminant onto a flow path of a food-transit system without adjusting a flowrate, the rotary introducer comprising: an inlet for receiving a trackable element and/or contaminant; an outlet which is positioned radially inwardly of the inlet and which is communicable with a food-transit conduit to discharge the trackable element and/or contaminant thereinto; a first rotatable member having a first device-contact surface which is movable between a first rotatable-member start position at or adjacent to the inlet and a first rotatable-member stop position; and a second rotatable member having a second device-contact surface which is movable between a second rotatable-member start position at or adjacent to the inlet and a second rotatable-member stop position at or adjacent to the outlet; the first rotatable-member start position and the second rotatable-member start position being angularly displaced from each other; the first rotatable-member stop position and second rotatable-member stop position being coincident or substantially coincident; the first and second device-contact surfaces opposing each other and defining a volume-adjustable device cavity; wherein, in a trackable-element receiving condition, the inlet is open to receive a trackable element and/or contaminant in the device cavity due to the first and second device-contact surfaces being at the angularly displaced first and second rotatable-member start positions respectively, and the outlet is closed by at least one of the first and second rotatable member; and in a trackable-element discharge condition, the outlet is open with the second device-contact surface being at the second rotatable-member stop position and the first device-contact surface being urged towards the first rotatable-member stop position such that a trackable-element discharge force is directed radially inwardly through the outlet to discharge the trackable element and/or contaminant from the device cavity, thus enabling the first device-contact surface to continue to the first rotatable-member stop position causing the outlet to close.

According to a sixth aspect of the invention, there is provided an introducer for introducing a trackable element and/or contaminant on or into a flow path of a food-transit system without or substantially without adjusting a flowrate, the introducer comprising: an inlet for receiving a trackable element and/or contaminant; an outlet which is spaced radially of the inlet and which is communicable with a food-transit conduit to discharge the trackable element and/or contaminant thereinto; and urging means for moving a trackable element and/or contaminant to be introduced to the flow path from the inlet and urged through the outlet without or substantially without in use adjusting a flowrate of an associated food-transit system.

In this aspect, the introducer may utilise one, more or a combination of the features of the first or fifth aspects of the invention.

BRIEF DESCRIPTION OF THE FIGURES

The invention will now be more particularly described, by way of example only, with reference to the accompanying drawings, in which.

DETAILED DESCRIPTION

Figure 1:
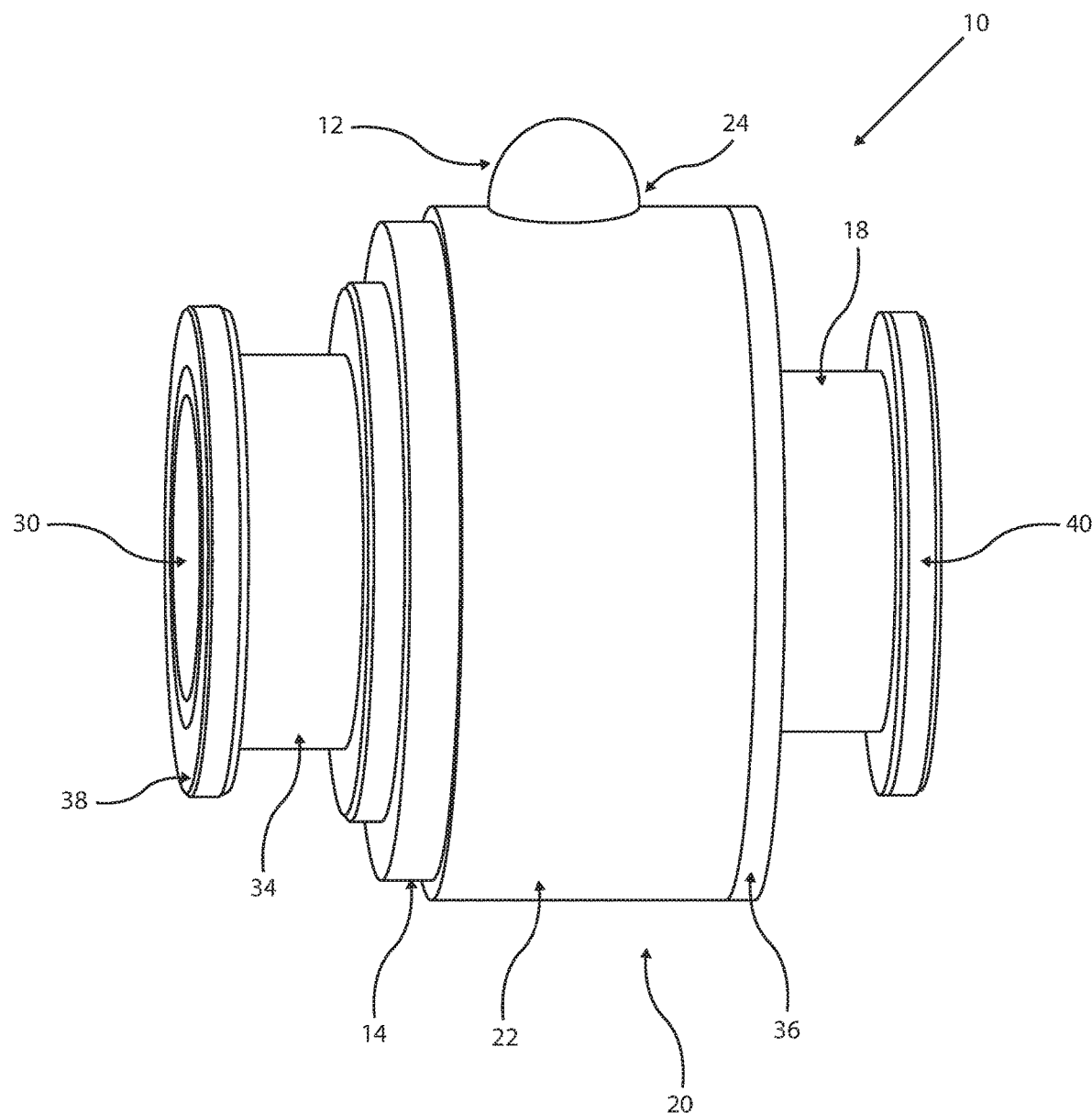
FIG. 1 shows a side representation of a first embodiment of a rotary introducer in accordance with the first aspect of the invention.

Referring to FIG. 1 there is illustrated a rotary introducer, indicated globally at 10 for the introduction of a trackable device 12, which in this case is a trackable element and/or contaminant, onto a flow path of a food-transit system without adjusting a flowrate of a liquid or semi-liquid foodstuff being transported therethrough.

Figure 2:
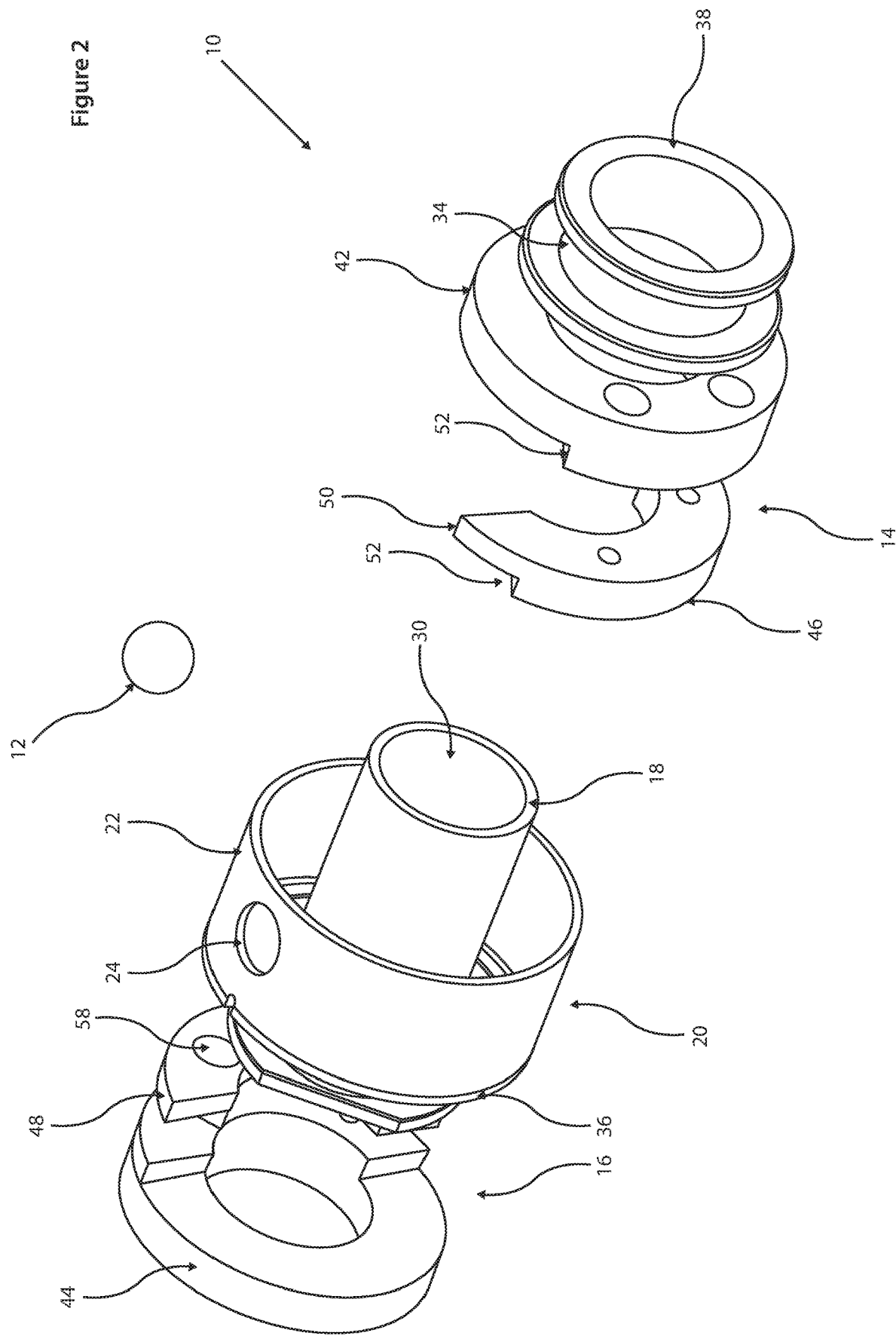
FIG. 2 shows an exploded perspective representation of the rotary introducer of FIG. 1.

The rotary introducer 10 comprises a rotatable driving member 14 and a rotatable drivable member 16 which are mutually co-operable with one another. These components can be seen in FIG. 2. The driving and drivable members 14, 16 are positionable about a food-transit conduit 18, which is here associated with, and may be preferably integrally formed with, an introducer housing 20 within which the driving and drivable members 14, 16 are housable so as to be rotatably movable about the food-transit conduit 18.

Figure 3:
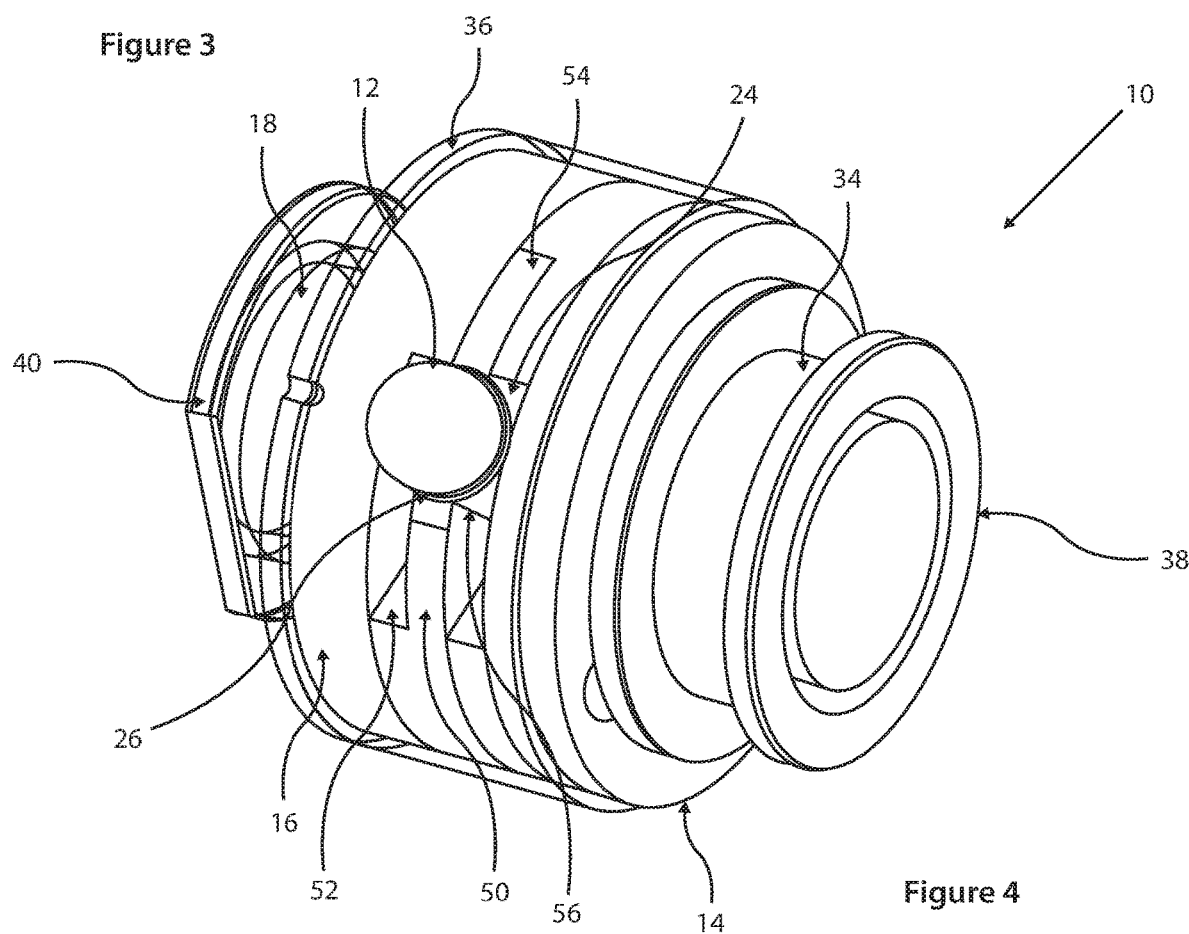
FIG. 3 shows a perspective representation of the rotary introducer of FIG. 1, the driving and drivable members being in their respective start positions, with an introducer housing of the rotary introducer being transparent for clarity.

On an external circumferential wall 22 of the introducer housing 20 is provided an inlet port 24, which permits access to an inlet 26 of the rotary introducer 10 when in a trackable-element receiving condition. This can be seen in FIG. 3; the circumferential wall 22 of the introducer housing being shown to be transparent to illustrate the inlet 26.

On a pipe body of the food-transit conduit 18 may be provided an outlet port 28 to allow the trackable device to be inserted into a flow path which passes through the bore 30 of the food-transit conduit 18. In a trackable-element discharge condition of the rotary introducer 10, an outlet 32 of the rotary introducer will open adjacent to the outlet port 28, and this will be discussed in detail below. Preferably, the inlet 26 and outlet 32 are angularly displaced from one another, preferably by between 90 and 180 degrees, with the outlet 32 being radially-inwardly disposed of the inlet 26.

The introducer housing 20 may be formed having an end cap 34 against which one or other of the driving and drivable member 14, 16 may abut, and the external circumferential wall 22 may extend around the full circumference of the food-transit conduit 18 to retain the driving and drivable members 14, 16 in position.

In the depicted embodiment, there is provided a housing flange portion 36 which is engagable around the food-transit conduit 18 and which abuts against the driving member 14 to retain it inside the introducer housing 20. This has an end flange 38 which allows the rotary introducer 10 as a whole to be coupled to a food-transit pipe network. An opposing end of the food-transit conduit 18 may also be formed so as to have a connecting flange 40.

In practice, the depicted embodiment of rotary introducer 10 indicates a simplified version of the introducer housing 20. The driving and drivable member 14, 16 are preferably encasable within an introducer housing, such that both of the driving and drivable member 14, 16 abut an end cap thereof. Bearings which couple to the end caps may be provided to improve the freedom of rotation of the driving and drivable members 14, 16 with respect to the introducer housing.

The introducer housing will also be provided with a means by which the driving member 14, at least, can be rotated, via a drive engagement means. This could be provided, for example by magnetic engagement with a magnetic drive, if the driving member 14 were sufficiently magnetic or magnetisable, or there could be a cut-out portion of the introducer housing 20 to allow for coupling of a ring gear associated with the driving member 14 to a gear-toothed coupling shaft, which could be in turn connected to a motor. Alternatively, the driving member 14 could be accessible to the user for manual actuation, as would be the case for the depicted embodiment.

The driving member 14 and drivable member 16 are formed as two parts of a hollow cylinder, preferably being formed such that each comprises a, preferably disciform, base portion 42, 44 and a, preferably substantially hemi-cylindrical, stepped portion 46, 48 which projects from the respective base portion 42, 44. In the depicted embodiment, the base portions 42, 44 and the stepped portions 46, 48 may be manufactured separately for simplicity, but it will be apparent that each of the driving and drivable members 14, 16 could be formed as a single unitary piece.

The driving member 14 is formed such that the stepped portion 46, when attached to the base portion 42, has a projecting armature 50 which preferably projects in a plane of the base portion 42 out of step wall 52 of the stepped portion 46, and the armature 50 preferably has a wedge- or triangular-shaped profile. In the depicted embodiment, there is space around either side of the projecting armature 50, but could feasibly be formed more as a shoulder projecting from the base portion 42.

The drivable member 16 is formed having a complementary shape to the driving member 14, such that the two stepped portions 46, 48 can be engaged together to complete the cylinder formed by the driving and drivable members 14, 16. The engagement of the base portion 44 and the stepped portion 48 of the drivable member 16 is such that a complementary recess 54 is formed within which the projecting armature 50 of the driving member 14 is receivable.

The receivable portions of the driving and drivable member 14, 16, which in this instance are the armature 50 and complementary recess 54, may be magnetically interengagable such that, when the armature 50 is received within the recess 54, the driving and drivable members 14, 16 latch to one another magnetically.

Whilst the driving and drivable members 14, 16 are described as forming a cylinder when engaged with one another, they do not completely tessellate; there is a mismatch between the sizes of the stepped portions 46, 48 which allows for rotation between the driving and drivable members 14, 16 to occur. This effectively forms a device cavity 56 within which the trackable device 12 can be introduced into the rotary introducer 10 during use. The device cavity 56 can be seen in particular in FIG. 3 of the drawings.

The specific arrangement of the driving and drivable members 14, 16 is such that the armature 50 of the driving member 14 is receivable within the complementary recess 54 of the drivable member 16. However, this need not be the case, and the reverse configuration could readily be considered, for example.

On the drivable member 16 a plurality of bearing receivers 58 can be seen; bearings may be provided to facilitate rotational engagement between the driving and drivable members 14, 16 of the rotary introducer 10. Similar and complementary bearing receivers may be provided on the driving member 14 if applicable.

Figure 4:
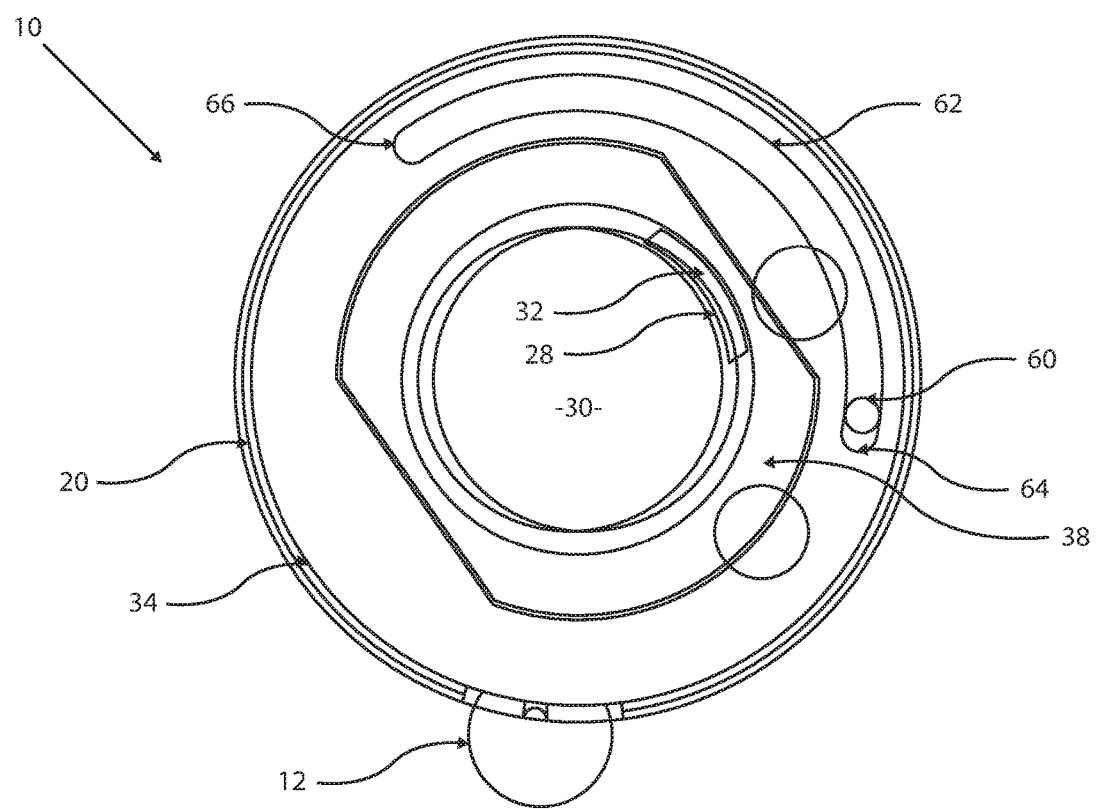
FIG. 4 shows an end view of the rotary introducer of FIG. 1, the introducer housing of the rotary introducer being transparent for clarity.

FIG. 4 shows the end cap 34 of the introducer housing 20. A projecting pin or stop 60 may be provided on the base portion 44 of the drivable member 16 which is engageable with a corresponding, preferably arcuate, slot 62 in the end cap 34. The correspondence between the stop 60 and slot 62 may define the rotational minimum and maximum positions for the drivable member 16, as the stop 60 abuts or is stopped by the first or second end 64, 66 of the slot 62.

In use, the rotary introducer 10 can be utilised to insert a trackable device 12 into a pipe of a food-transit system, preferably via the food-transit conduit 18. The process by which this occurs is depicted in detail in FIGS. 5a to 5i. A cross-section through the rotary introducer 10 is illustrated in each case, with the positions of the respective stepped portions 46, 48 of the driving and drivable members 14, 16 being visible in each case.

At one end 68, 70 of each stepped portion 46, 48, the surfaces are complementarily shaped, such that the driving member 14 can engage with the drivable member 16. These ends 68, 70 may be aligned to a radius of the rotary introducer 10, as illustrated. At the opposing ends of the stepped portions 46, 48 are the armature 50 and complementary recess 54 respectively. The outermost surface of each respectively forms first and second device-contact surfaces 72, 74.

Figure 5A:
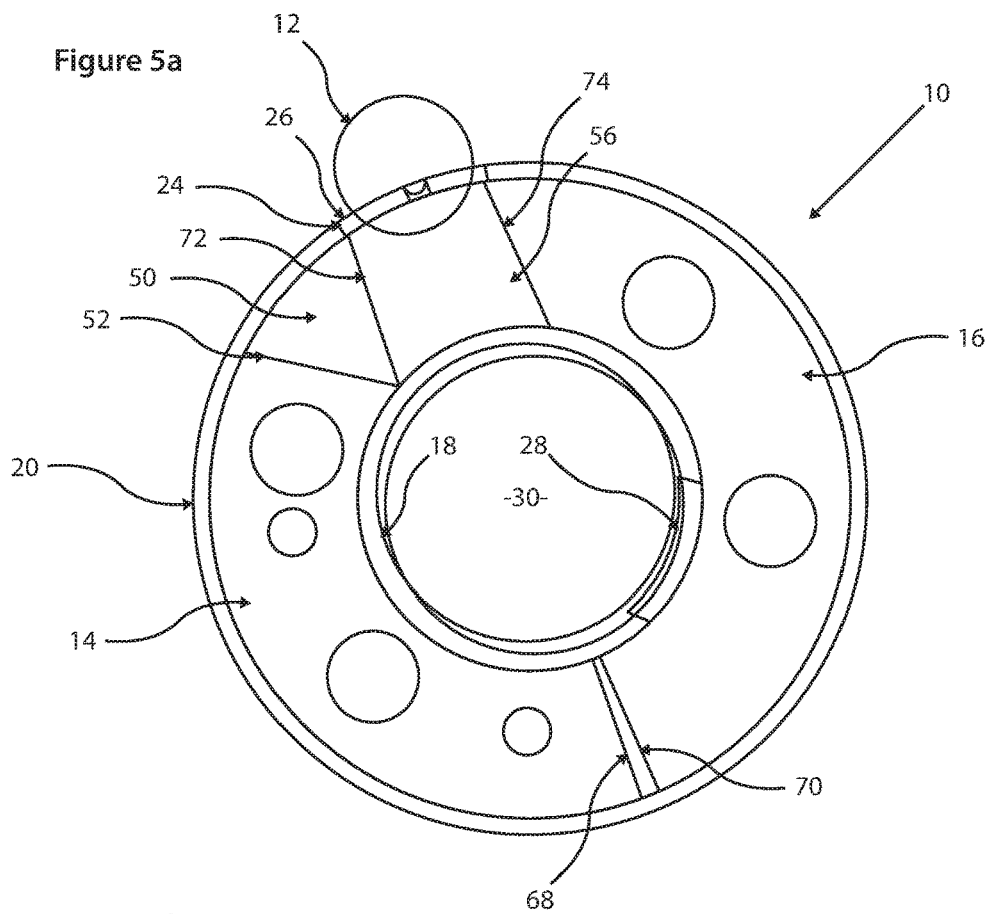
FIG. 5a shows a diametric cross-section through the rotary introducer of FIG. 1, indicating the trackable element and/or contaminant being inserted into the inlet of the rotary introducer in the trackable-element receiving condition.

In FIG. 5a, the inlet 26 is open to receive the trackable device 12 in the device cavity 56 due to the first and second device-contact surfaces 72, 74 of the driving and drivable members 14, 16 being in angularly displaced driving-member and drivable-member start positions respectively, with the outlet is closed by at least one of the driving and drivable member 14, 16, here the drivable member 16. FIG. 5a therefore represents a trackable-element receiving condition of the rotary introducer 10, with the driving and drivable members 14, 16 having the first and second device-contact surfaces 72, 74 respectively in driving-member and drivable-member start positions to define the inlet 26. The inlet 26 is, in the depicted embodiment, aligned with the inlet port 24 of the introducer housing 20.

Figure 5B:
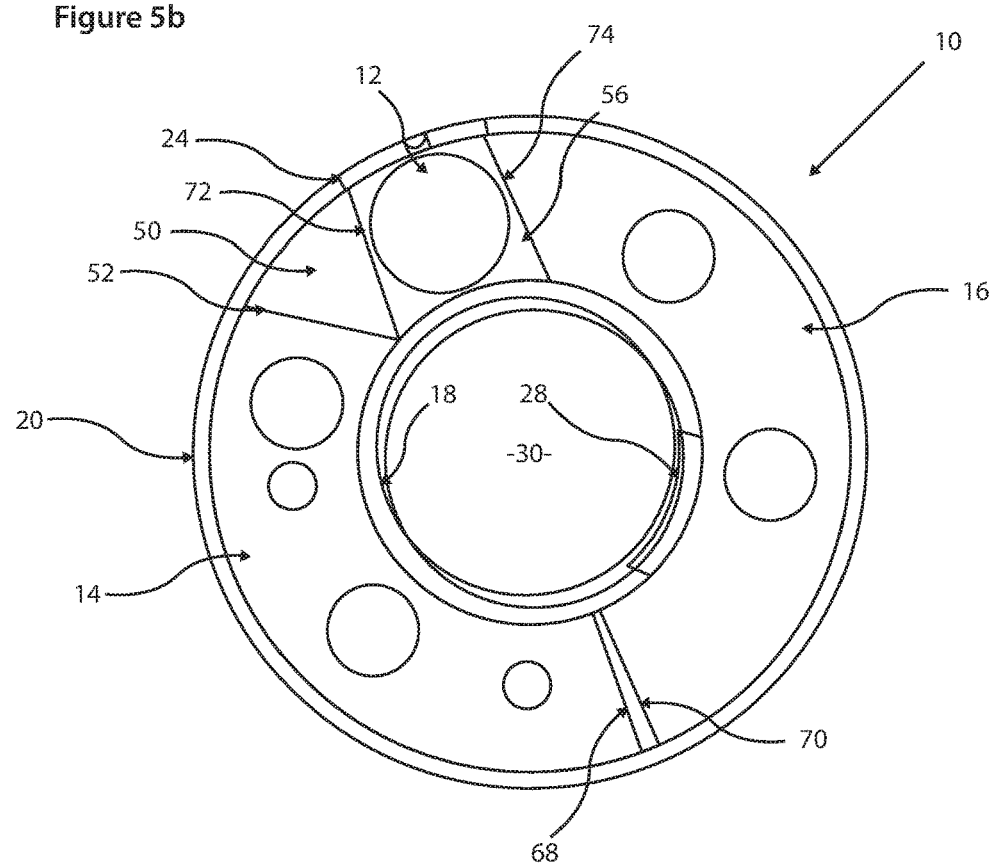
FIG. 5b shows a diametric cross-section through the rotary introducer of FIG. 1, indicating the trackable element and/or contaminant having been received in the device cavity.

In FIG. 5b, the trackable device 12 has been introduced into the device cavity 56, and the first and second device-contact surfaces 72, 74 are positioned so as to be in contact or near-contact with the sides of the trackable device 12.

Figure 5C:
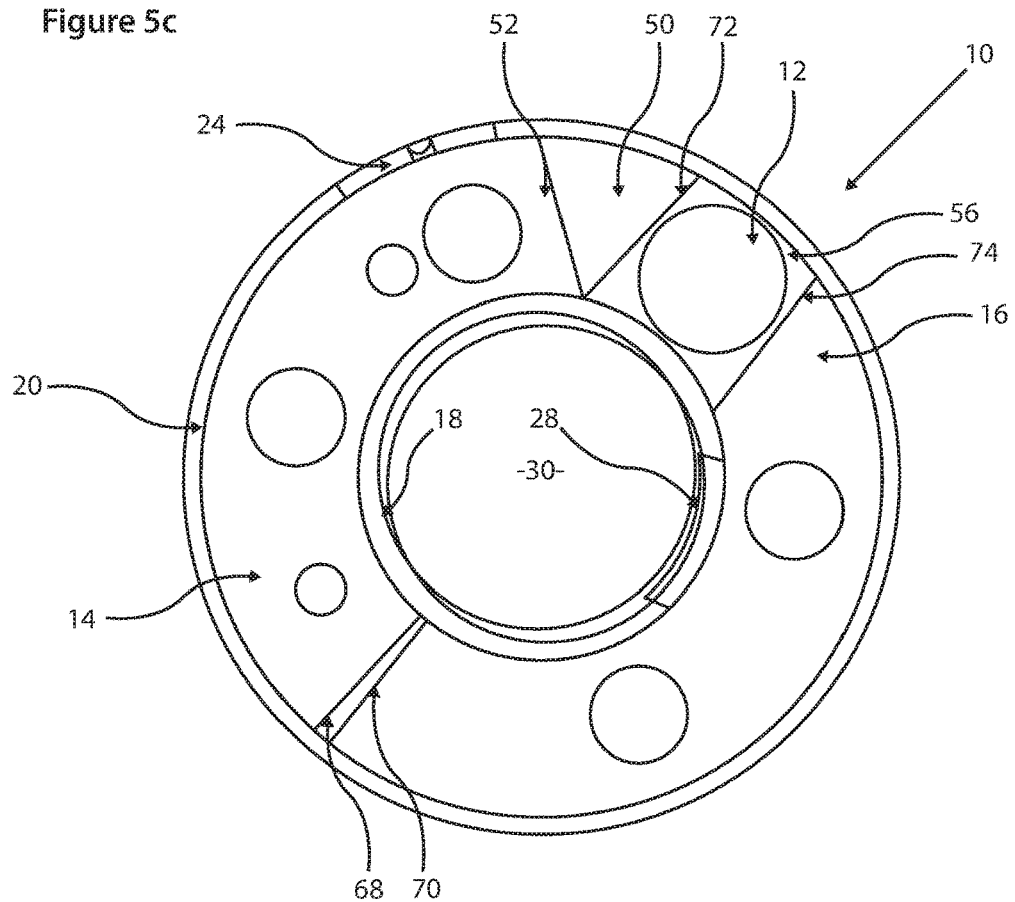
FIG. 5c shows a diametric cross-section through the rotary introducer of FIG. 1, following a clockwise rotation of the driving member of the rotary introducer.

FIG. 5c shows a clockwise rotation of the driving member 14. The trackable device 12, having been received into the device cavity 56, is sandwiched between the first and second device-contact surfaces 72, 74, such that a rotational force is imparted from the driving member 14 through the trackable device 12 to the drivable member 16. Driving the driving member 14 therefore results in an indirect actuation of the drivable member 16.

Figure 5D:
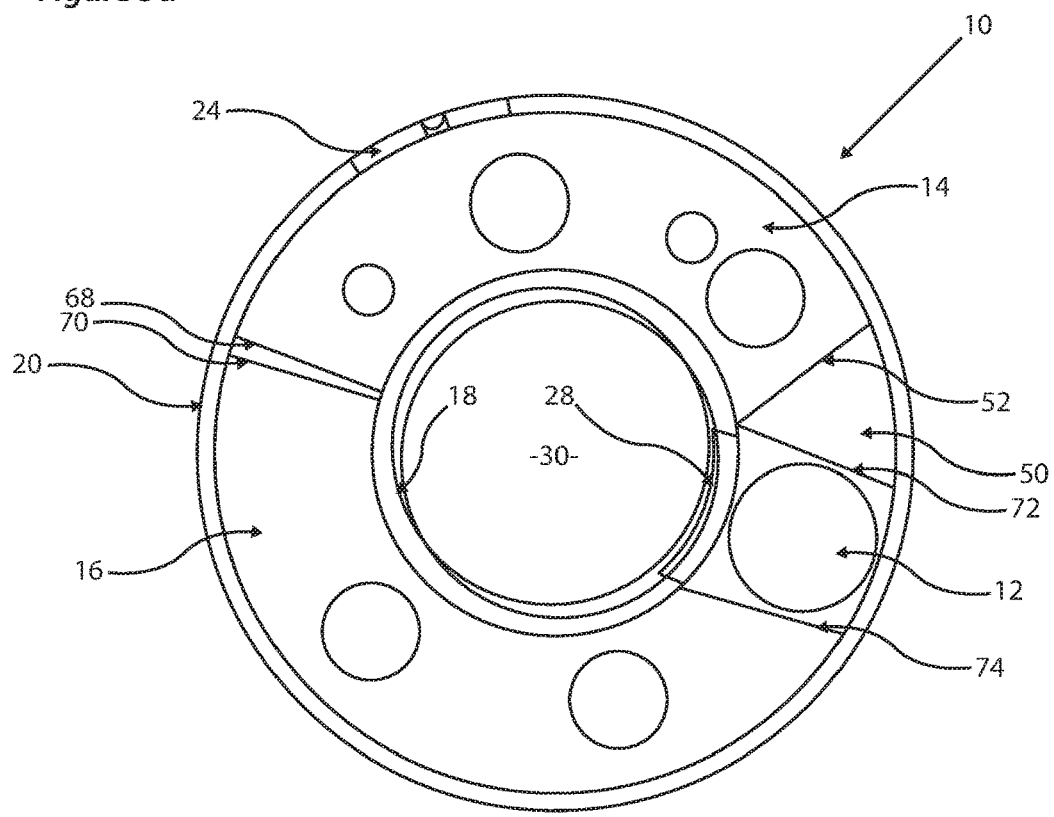
FIG. 5d shows a diametric cross-section through the rotary introducer of FIG. 1, following a further clockwise rotation of the driving member of the rotary introducer, such that the rotary introducer is in the trackable-element discharge condition.
Figure 5E:
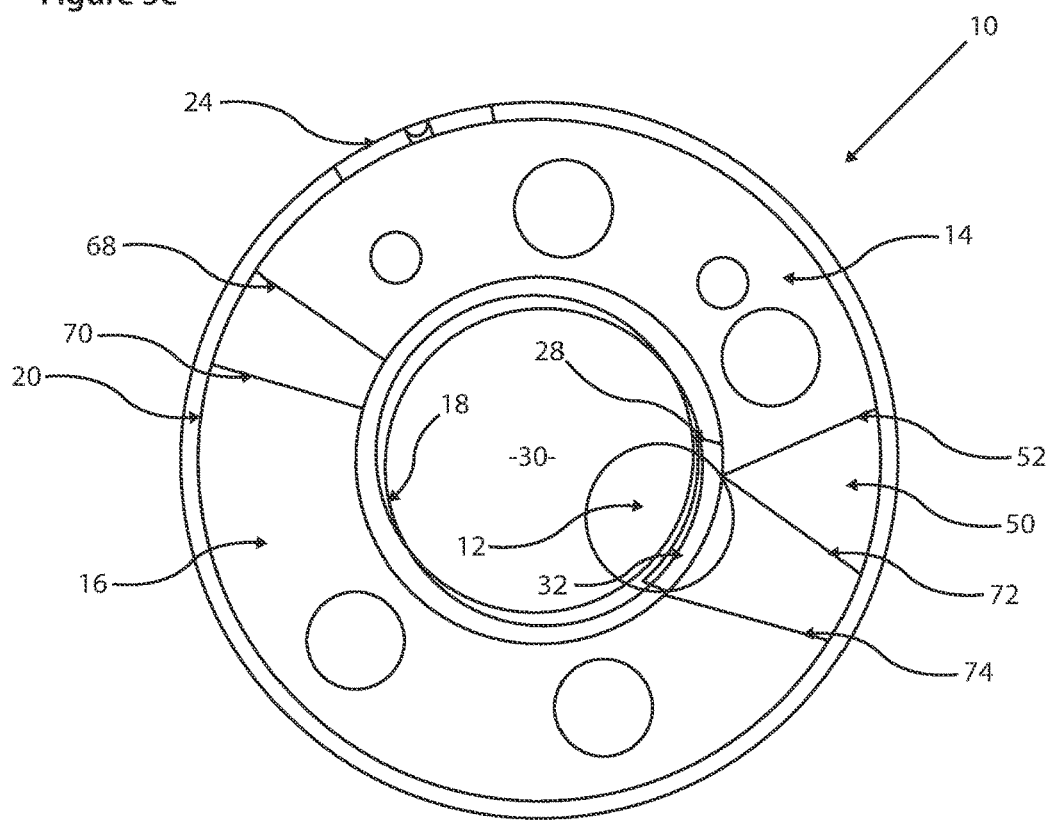
FIGS. 5e and 5f show diametric cross-sections through the rotary introducer of FIG. 1, following incremental sequential clockwise rotations of the driving member of the rotary introducer.

A further clockwise rotation of the driving member 14 is illustrated in FIG. 5d. In this configuration, however, the drivable member 16 has rotated sufficiently that the stop 60 of the drivable member 16 (as shown in FIG. 4) will have contacted the first end 64 of the slot 62 of the introducer housing 20, preventing further clockwise rotation of the drivable member 16. This represents a drivable-member stop position.

On the other hand, there is no static impediment to the clockwise motion of the driving member 14 provided that a driving force continues to be applied. The trackable device 12 offers some physical resistance; however, the shapes of the first and second device-contact surfaces 72, 74 are such that a trackable-element discharge force is applied to the trackable device 12 in a radially-inward direction, towards and through the outlet 32 and/or outlet port 28 as the first and second device-contact surfaces 72, 74 are brought into coincidence.

This trackable-element discharge force is achieved here by providing the first and second device-contact surfaces 72, 74 so as to be radially convergent, that is, substantially forming a substantially trapezoidally-shaped device cavity 56 of decreasing volume as the first device-contact surface 72 advances towards the second device-contact surface 74. This provides a simple way of creating a radially-inwardly directed force to push or urge the trackable device 12 through the outlet 32. This can be readily seen in FIG. 5e.

Figure 5F:
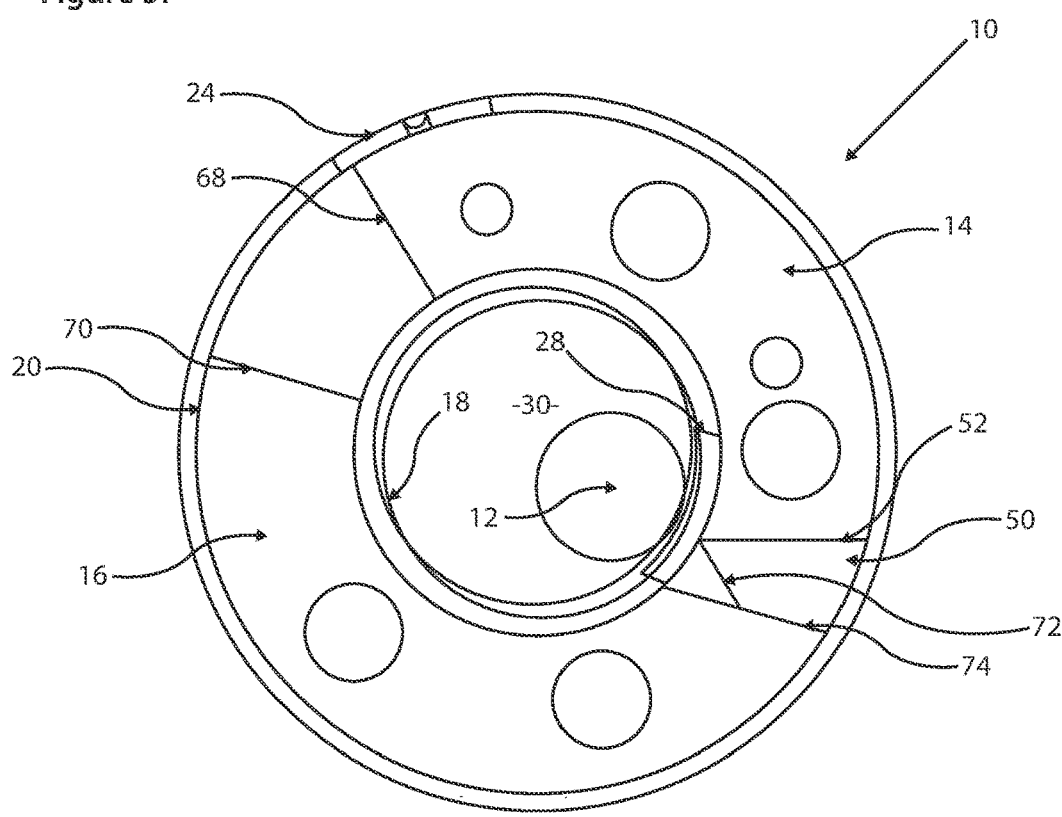

With the trackable device 12 discharged into the food-transit conduit 18, as illustrated in FIG. 5f, the driving member 14 can continue to rotate in a clockwise direction. The projecting armature 50 is received into the complementary recess 54 of the drivable member 16, which allows for continued rotation of the driving member 14. FIG. 5f therefore indicates a trackable-element discharge condition of the rotary introducer 10, since the first and second device-contact surfaces 72, 74 are or are substantially coincident with one another.

Figure 5G:
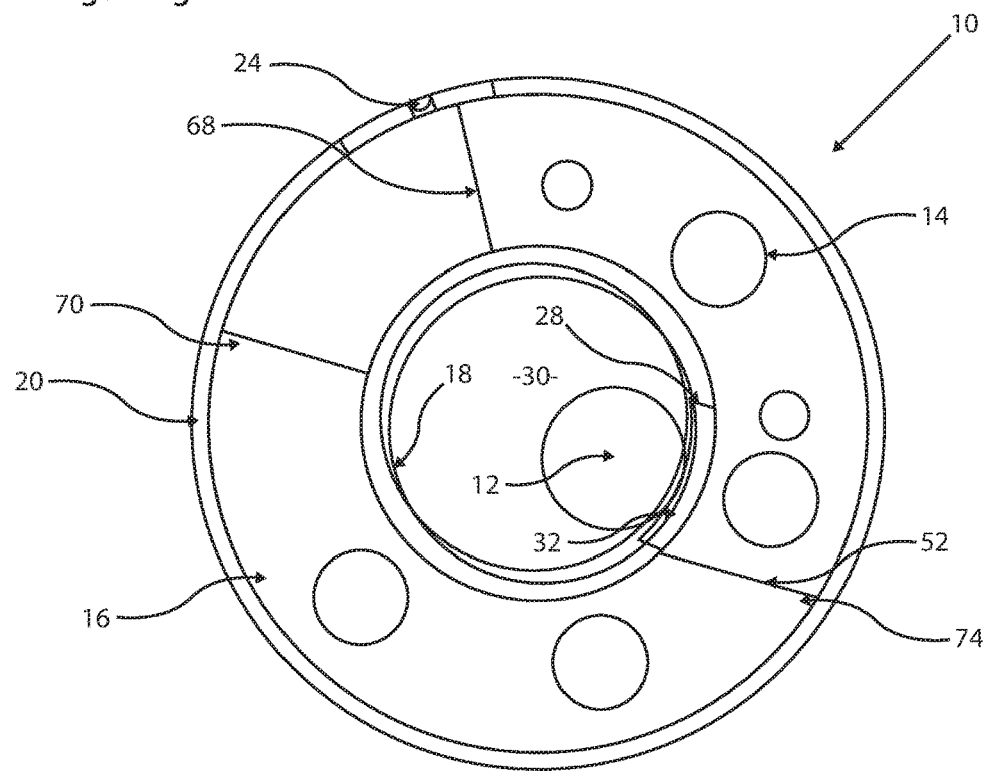
FIG. 5g shows a diametric cross-section through the rotary introducer of FIG. 1, following complete clockwise rotation of the driving member such that the first and second device-contact surfaces are coincident.

A continued rotation of the driving member 14, as shown in FIG. 5g, results in closure of the outlet 32 of the rotary introducer 10. This prevents or limits reflux of foodstuffs from the food-transit conduit 18 into the device cavity 56. Here the step wall 52 of the driving member 14 abuts the second device-contact surface 74 of the drivable member 16, preventing further clockwise rotation of the driving member 14. This therefore represents a driving-member stop position for the driving member 14, in which the outlet 32 is closed.

Preferably, the driving and drivable members 14, 16 will engage with one another at this point, and this may be achieved by magnetic coupling of the driving and drivable members 14, 16. This allows for the driving and drivable members 14, 16 to be rotated in an anti-clockwise direction together, without necessarily providing a physical coupling between the two. The anti-clockwise rotation of the driving member 14 effectively pulls the magnetically-engaged drivable member 16 in an anti-clockwise direction. This can be seen in FIG. 5h, and shows how the outlet port 28 remains closed despite the anti-clockwise rotation of the driving and drivable members 14, 16.

It is noted that a recoil or return mechanism may be provided which is different to the driving means by which the driving member 14 is actuated, such as a coiled-spring return element. Such an arrangement would allow for a unidirectional drive means to be provided to actuate the driving member 14 in a clockwise direction, such as a worm gear.

Figure 5H:
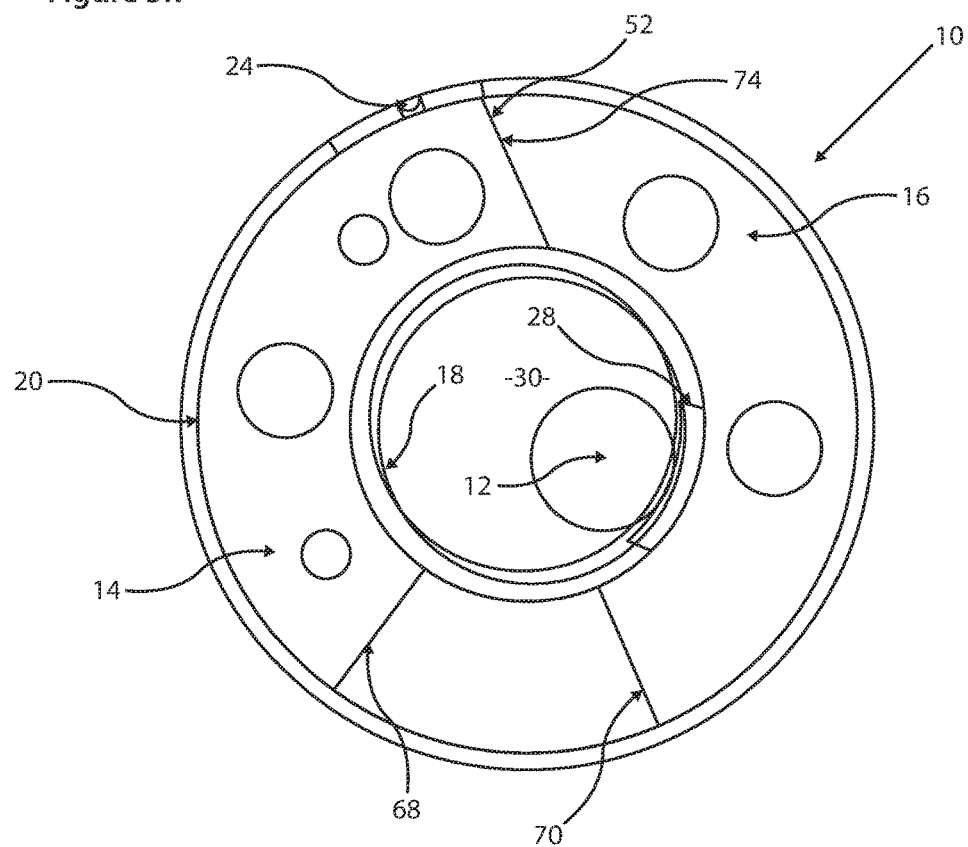
FIG. 5h shows a diametric cross-section through the rotary introducer of FIG. 1, following anti-clockwise rotation of the driving member in co-operation with the drivable member.
Figure 5I:
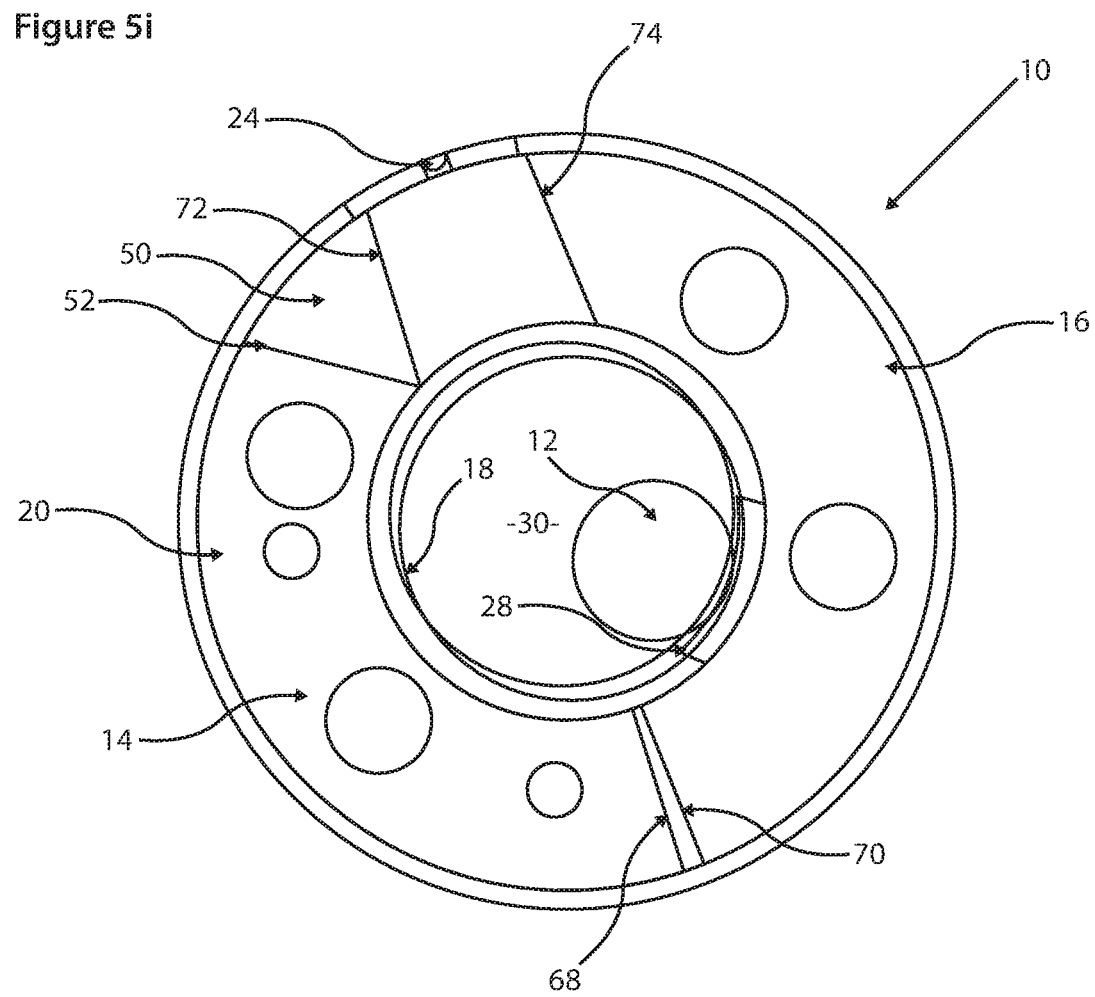
FIG. 5i shows a diametric cross-section through the rotary introducer of FIG. 1, following further anti-clockwise rotation of the driving member having released the drivable member, to return the rotary introducer to the trackable-element receiving condition.

The position of the drivable member 16 in FIG. 5h represents a return to the drivable-member start position; the stop 60 of the drivable member 16 is now in contact with the second end 66 of the slot 62 of the introducer housing 20, and therefore further anti-clockwise rotation is prevented. Continued anti-clockwise rotation of the driving member 14 therefore disengages the magnetic connection between the driving and drivable members 14, 16. This can be seen in FIG. 5i, in which the driving member 14 has been returned to the driving-member start position, having de-latched from the drivable member 16 which remains in the drivable-member start position. The rotary introducer 10 is now in a suitable condition for insertion of another trackable device 12, without the flow of the food-transit system having been interrupted.

To integrate the rotary introducer 10 into a food-transit system, a pipe of a food-transit pipe network could be replaced with the food-transit conduit 18 of the rotary introducer 10. Alternatively, the food-transit conduit could be dispensed with, and the driving and drivable members 14, 16 could be coupled directly around an existing pipe of the food-transit pipe network which has an outlet.

It may also be possible to engage the rotary introducer 10 into a suitable section of a food-transit pipe network in a manner which enables ready access for cleaning and maintenance. For example, the end and connecting flanges 36, 38 may be provided so as to be magnetically-engagable with corresponding flanges on the food-transit pipe network.

Figure 6:
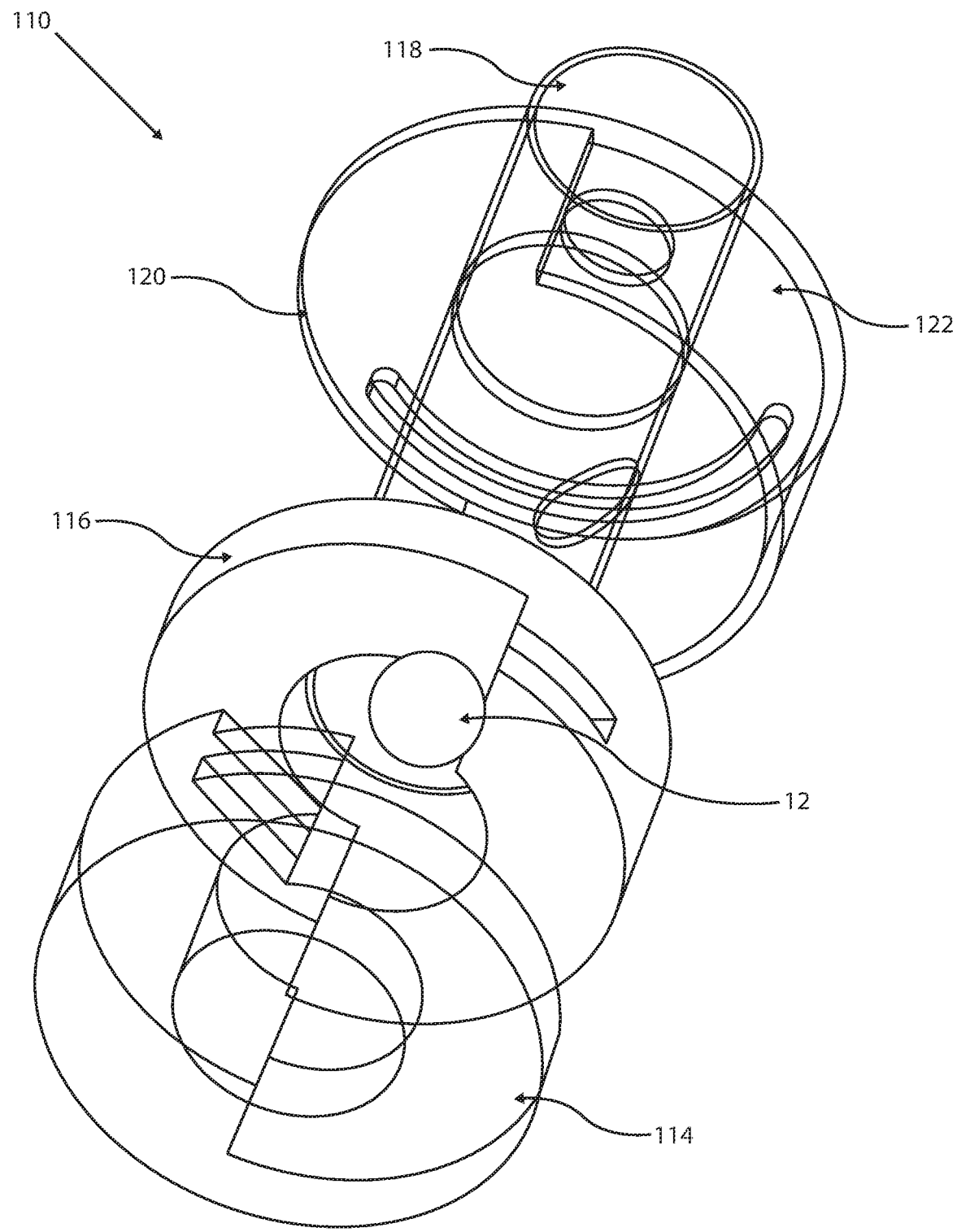
FIG. 6 shows a perspective representation of a second embodiment of a rotary introducer in accordance with the first aspect of the invention.

A second embodiment of a rotary introducer is illustrated in FIG. 6, and is indicated globally at 110. Identical or similar components to that of the first aspect of the invention are referred to using identical or similar reference numerals, and further detailed description is therefore omitted for brevity.

This embodiment of rotary introducer 110 is largely similar to that of the first embodiment, other than the driving and drivable members 114, 116 are unitarily formed, for example, being moulded from a single piece of plastics material, or could be 3D printed.

Furthermore, the introducer housing 120 is sized so as to only cover part of the driving and drivable members 114, 116 about the food-transit conduit 118; the circumferential wall 122 extends around approximately 180 degrees about the food-transit conduit 118, which provides a greater degree of access to the driving and drivable members 114, 116. Such an arrangement may therefore be more suitable for manual actuation of the driving member 114 in particular.

Whilst the embodiments described above assume that rotational force will be imparted to the driving member of the rotary introducer, it will be appreciated that a similar result could be achieved by the provision of a synchronised driving force for each of the driving and drivable members. Such an arrangement would potentially eliminate the need for the pin or stop to be present on the drivable member, and potentially would permit a much wider range of introducer housings to be considered.

It is also noted that the mechanism by which the rotational minimum and maximum positions of the drivable member is created may not necessarily be provided by a stop. For example, a lip or rim inside the introducer housing could be used to limit the rotational movement of the drivable member. Additionally, as discussed above, the provision of a synchronised driving force could also remove the need for a stop entirely.

Magnetic latching between the driving and drivable members is not the only means by which the reversing of the rotary introducer may be achieved. For example, the return mechanism alluded to above could be coupled directly to the drivable member to encourage return to the drivable member start position in use.

Although rotatable driving and drivable members are suggested and described hereinbefore, any other suitable urging means or urging mechanism, preferably being rotatable but not necessarily limited to such, may be considered. For example, a plunger mechanism to press the trackable element/contaminant into the flowing food stuff, and/or a compressed-gas discharge mechanism to fire the trackable element/contaminant into the flowing food stuff may be feasibly considered. In these instances, it may be beneficial to have a discharge conduit at an acute angle to the direction of flow of the flow path to prevent or limit the ingress of flowing food stuff It is therefore possible to provide a rotary introducer which is capable of introducing a trackable element and/or contaminant into a food-transit system without adjusting a flowrate of the system. This can be achieved by the provision of first and second rotatable members, which are preferably a master and slave, driving and drivable members respectively. The trackable element and/or contaminant can be clasped between the two rotatable members in such a manner as to encourage insertion of the trackable element and/or contaminant into the flow path of the food-transit system once aligned with an outlet of the rotary introducer. Continued rotation of the rotatable members then allows the outlet to be shut off, without resulting in reflux of the material in the food-transit system back into the rotary introducer.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

What is claimed is:

1. A rotary introducer configured for introducing a trackable element and/or contaminant on or into a flow path of a food-transit system without adjusting a flowrate, the rotary introducer comprising:
   an inlet configured for receiving a trackable element and/or contaminant;
   an outlet which is positioned radially inwardly of the inlet and which is communicable with a food-transit conduit to discharge the trackable element and/or contaminant thereinto;
   a rotatable driving member having a first device-contact surface which is movable between a driving-member start position at or adjacent to the inlet and a driving-member stop position; and
   a rotatable drivable member having a second device-contact surface which is movable between a drivable-member start position at or adjacent to the inlet and a drivable-member stop position at or adjacent to the outlet;
   the driving-member start position and the drivable-member start position being angularly displaced from each other;
   the driving-member stop position and drivable-member stop position being coincident;
   the first and second device-contact surfaces opposing each other and defining a volume-adjustable device cavity;
   wherein, in a trackable-element receiving condition, the inlet is open to receive a trackable element and/or contaminant in the device cavity due to the first and second device-contact surfaces being at the angularly displaced driving-member and drivable-member start positions respectively, and the outlet is closed by at least one of the driving and drivable members; and in a trackable-element discharge condition, the outlet is open with the second device-contact surface being at the drivable-member stop position and the first device-contact surface being urged towards the driving-member stop position such that a trackable-element discharge force is directed radially inwardly through the outlet to discharge the trackable element and/or contaminant from the device cavity, thus enabling the first device-contact surface to continue to the driving-member stop position causing the outlet to close.

2. The rotary introducer as claimed in claim 1, wherein the driving member includes a drive engagement means.

3. The rotary introducer as claimed in claim 2, wherein the drive engagement means comprises a magnetically driveable portion.

4. The rotary introducer as claimed in claim 2, wherein the drive engagement means comprises a driveable ring gear.

5. The rotary introducer as claimed in claim 1, wherein the drivable member includes a recess in the second device-contact surface, the driving member having an armature upon which the first device-contact surface is positioned which is receivable within the recess.

6. The rotary introducer as claimed in claim 5, wherein the armature is wedge-shaped.

7. The rotary introducer as claimed in claim 1, wherein the first and second device-contact surfaces are radially convergent with respect to one another.

8. The rotary introducer as claimed in claim 7, wherein the first and second device-contact surfaces form a triangular wedge to create the trackable-element discharge force.

9. The rotary introducer as claimed in claim 1, further comprising an introducer housing which at least partially encloses the driving and/or drivable member.

10. The rotary introducer as claimed in claim 9, wherein the introducer housing includes an inlet port which is aligned with the inlet in the trackable-element receiving condition.

11. The rotary introducer as claimed in claim 9, wherein the introducer housing is integrally formed with a food-transit conduit.

12. The rotary introducer as claimed in claim 9, wherein the drivable member includes a projecting stop, the introducer housing including a stop-receiving slot with which the stop is engagable, the stop defining the drivable-member start and stop positions.

13. The rotary introducer as claimed in claim 1, wherein the driving and drivable members are at least in part magnetically engagable.

14. The rotary introducer as claimed in claim 13, wherein the driving and drivable members are adapted to magnetically engage when the first device-contact surface reaches the driving-member stop position to allow counter-rotation of the rotary introducer without opening the outlet.

15. The rotary introducer as claimed in claim 1, further comprising a pipe element about which the driving and drivable members are rotationally movable, the pipe element having magnetic engagement elements at opposing longitudinal ends thereof for magnetic connection to a food-transit system.

16. The rotary introducer as claimed in claim 1, further comprising a reset mechanism to return the driving and drivable members to the driving-member and drivable-member start positions respectively following discharge of a trackable element and/or contaminant.

17. A food-transit system for the transit of liquid or semi-liquid foodstuffs, the food transit system comprising: a food-transit pipe network defining a flow path therethrough; a rotary introducer as claimed in claim 1; and a trackable and/or contaminant; wherein the rotary introducer is introducible onto the flow path of the food-transit pipe network to permit introduction of the trackable element and/or contaminant into the flow path without adjusting a flowrate of foodstuffs through the food-transit pipe network.

18. A method of introducing a trackable element and/or contaminant into a food-transit system without adjusting a flowrate of foodstuffs therethrough, the method comprising the steps of:
a] providing a rotary introducer as claimed in claim 1 at or adjacent to an inlet to a food-transit pipe network of the food-transit system;
b] inserting a trackable element and/or contaminant into a device cavity of the rotary introducer whilst in the trackable-element receiving condition;
c] rotating the driving member of the rotary introducer into the trackable-element discharge condition so as to align the trackable element and/or contaminant with the outlet; and
d] continuing to rotate the driving member of the rotary introducer to create the trackable-element discharge force to urge the trackable element and/or contaminant into the inlet to the food-transit pipe network and close the outlet.

19. The method as claimed in claim 18, wherein during step d] the first and second device-contact surfaces form a wedge of decreasing area to create the trackable-element discharge force.

20. The method as claimed in claim 18, further comprising a step e] subsequent to step d] of counter-rotating the driving member to return the rotary introducer to the trackable-element receiving condition.

* * * * *